US012697213B2

(12) United States Patent
Stappenbeck et al.

(10) Patent No.: US 12,697,213 B2
(45) Date of Patent: Aug. 4, 2026

(54) PROSTHESIS CONNECTING DEVICE

(71) Applicant: TRICARES SAS, Paris (FR)

(72) Inventors: Nadine Stappenbeck, Munich (DE); Brian Murphy, Kilcolgan (IE); Helmut Straubinger, Aschheim (DE)

(73) Assignee: TRICARES SAS, Paris (FR)

( * ) Notice: Subject to any disclaimer, the term of this patent is extended or adjusted under 35 U.S.C. 154(b) by 946 days.

(21) Appl. No.: 17/312,200

(22) PCT Filed: Dec. 17, 2019

(86) PCT No.: PCT/EP2019/085784
§ 371 (c)(1),
(2) Date: Jun. 9, 2021

(87) PCT Pub. No.: WO2020/127372
PCT Pub. Date: Jun. 25, 2020

(65) Prior Publication Data
US 2022/0047386 A1     Feb. 17, 2022

(30) Foreign Application Priority Data

Dec. 20, 2018     (EP) ..................................... 18214967

(51) Int. Cl.
*A61F 2/24*          (2006.01)
*A61F 2/95*          (2013.01)
*A61F 2/962*         (2013.01)
*A61F 2/966*         (2013.01)

(52) U.S. Cl.
CPC .......... *A61F 2/2436* (2013.01); *A61F 2/9522* (2020.05); *A61F 2/962* (2013.01); *A61F 2002/9665* (2013.01); *A61F 2220/0025* (2013.01)

(58) Field of Classification Search
CPC ...... A61F 2/2436; A61F 2/9522; A61F 2/962; A61F 2002/9665; A61F 2220/0025; A61F 2/2439
See application file for complete search history.

(56) References Cited

U.S. PATENT DOCUMENTS

| | | | |
|---|---|---|---|
| 5,749,921 | A | 5/1998 | Lenker et al. |
| 5,840,081 | A | 11/1998 | Andersen et al. |
| 8,070,800 | B2 | 12/2011 | Lock et al. |
| 9,782,256 | B2 | 10/2017 | Zeng |
| 10,039,639 | B2 | 8/2018 | Marchand et al. |
| 10,952,851 | B2 | 3/2021 | Marchand |

(Continued)

FOREIGN PATENT DOCUMENTS

| | | |
|---|---|---|
| EP | 3071151 B2 | 7/2017 |
| WO | 2001/064137 A1 | 9/2001 |

(Continued)

OTHER PUBLICATIONS

International Search Report and Written Opinion, Application No. PCT/EP2019/085784 dated Mar. 12, 2020.

*Primary Examiner* — Yashita Sharma
*Assistant Examiner* — Kia Xiong White
(74) *Attorney, Agent, or Firm* — The Dobrusin Law Firm, P.C.

(57) ABSTRACT

The invention relates to a connector device and a method for loading a prosthesis onto a delivery system as well as a method for delivery of the prosthesis and optionally retrieval of the prosthesis.

20 Claims, 11 Drawing Sheets

100

(56)　　　　References Cited

U.S. PATENT DOCUMENTS

| | | |
|---|---|---|
| 2004/0049207 A1 | 3/2004 | Goldfarb et al. |
| 2004/0186563 A1 | 9/2004 | Lobbi |
| 2005/0137697 A1 | 6/2005 | Salahieh |
| 2006/0020327 A1 | 1/2006 | Lashinski |
| 2007/0005129 A1 | 1/2007 | Damm et al. |
| 2007/0244552 A1 | 10/2007 | Salahieh |
| 2007/0270679 A1 | 11/2007 | Nguyen et al. |
| 2008/0086107 A1 | 4/2008 | Roschak |
| 2009/0005863 A1 | 1/2009 | Goetz |
| 2009/0054976 A1 | 2/2009 | Tuval et al. |
| 2010/0022948 A1 | 1/2010 | Wilson et al. |
| 2010/0256754 A1 | 10/2010 | Styre |
| 2010/0292779 A1 | 11/2010 | Straubinger et al. |
| 2011/0029072 A1 | 2/2011 | Gabbay |
| 2011/0046712 A1 | 2/2011 | Melsheimer et al. |
| 2011/0160836 A1 | 6/2011 | Behen |
| 2012/0083874 A1 | 4/2012 | Dale et al. |
| 2012/0209122 A1 | 8/2012 | Garbini et al. |
| 2013/0204357 A1 | 8/2013 | Thill et al. |
| 2013/0274855 A1 * | 10/2013 | Stante .................. A61F 2/2436 |
| | | 623/1.11 |
| 2013/0304200 A1 | 11/2013 | McLean et al. |
| 2014/0005767 A1 * | 1/2014 | Glazier ................. A61F 2/2418 |
| | | 623/2.11 |
| 2014/0144000 A1 | 5/2014 | Creaven et al. |
| 2014/0303719 A1 | 10/2014 | Cox |
| 2014/0331475 A1 | 11/2014 | Duffy et al. |
| 2017/0290661 A1 | 10/2017 | Von Segesser |
| 2018/0325667 A1 | 11/2018 | Gallagher et al. |
| 2020/0008941 A1 | 1/2020 | Stappenceck et al. |
| 2020/0360141 A1 | 11/2020 | Stappenceck et al. |

FOREIGN PATENT DOCUMENTS

| | | |
|---|---|---|
| WO | 2006/128185 A2 | 11/2006 |
| WO | 2008/118481 A1 | 10/2008 |
| WO | 2009/106545 A1 | 9/2009 |
| WO | 2009/137712 A1 | 11/2009 |
| WO | 2012/178115 A2 | 12/2012 |
| WO | 2013/104721 A1 | 7/2013 |
| WO | 2015/107226 A1 | 7/2015 |
| WO | 2016/090025 A1 | 6/2016 |
| WO | 2017/195125 A1 | 11/2017 |
| WO | 2020/127293 A1 | 6/2020 |

* cited by examiner

PROSTHESIS CONNECTING DEVICE

CLAIM OF PRIORITY

This application is a national phase filing under 35 USC § 371 from PCT Patent Application serial number PCT/EP2019/085784 filed on Dec. 17, 2019, and published as WO 2020/0127372 A1 on Jun. 25, 2020, which claims priority to European Patent Application Number EP 18214967.4 filed on Dec. 20, 2018. PCT Patent Application serial number PCT/EP2019/085784 and European Patent Application Number EP 18214967.4 are each incorporated by reference herein in its entirety.

FIELD

The invention relates to a connector device and a method for loading a prosthesis onto a delivery system as well as a method for delivery of the prosthesis and optionally retrieval of the prosthesis.

BACKGROUND

In the last decades minimally invasive techniques have advanced and are now possible in many medical fields.

In recent years the treatment of heart valve diseases and defects has become more and more successful. Examples are transapical, transjugular and transfemoral procedures for heart valve replacement therapies, e.g. aortic and mitral heart valve treatments.

In many cases a stent-based prosthesis with a tissue based replacement valve, e.g. pericard, is used and implanted to replace the endogenous heart valve by way of a catheter or delivery system.

The prosthesis has to be crimped and loaded onto the delivery system and a number of systems have been described in the art.

In the course of the loading procedure the stent or prosthesis is connected with a part of the delivery system. During deployment of the stent or prosthesis the stent or prosthesis is disconnected from the delivery system and fully released therefrom in order to be positioned to a target site.

Heart valve prostheses with self-expandable stents get crimped to their target diameter and are held in that crimped state by a delivery system shaft, which is advanced over the crimped prosthesis. As prosthesis deployment is usually carried out gradually, the section being deployed last is secured in a stent holder. This prevents premature deployment, which results from the radial force exerted by the partially deployed stent/prosthesis. Self-expandable prostheses of commercially available TAVI devices use that technique, e.g. Corevalve Medtronic, etc. The known procedures imply however various disadvantages which have so far not been solved in a satisfactory manner.

The technical problem with current stent holder designs is the difficulty of engaging several eyelets with the stent holder during the loading procedure. The eyelets need to be crimped to the diameter of the stent holder, which has a recess or receiving means for each eyelet. Each eyelet needs to be placed in its recess and the position must be maintained while the catheter shaft is advanced over the stent holder to secure the eyelets. The more eyelets there are, the more difficult to maintain them in their position while advancing the catheter shaft. As the eyelets are equally distributed around the circumference there is typically always one eyelet on the bottom of the stent holder, which is not visible to the operator. The not visible eyelet is difficult to control and can easily disengage. If a disengagement of the eyelet(s) occurs this step of the loading procedure needs to be restarted.

More so, the manual manipulation in the known manner by holding connecting means down and to introduce them from outside into the receiving means on a catheter are the more difficult the more connecting means are involved. This is to say if three eyelets are to be engaged with the receiving means it is already difficult to engage and keep these parts engaged and the step of covering them by the outer shaft of the catheter implies not only a high level of difficulty but also the danger of damage to the outer shaft. Such a damage and possible widening of the diameter or damaging the sharp edges of the end of the shaft implies problems in the following procedure of introducing the catheter into the patient by way of an introduction port or during advancing of the catheter in a vessel. All parts of the prosthesis capsule carrying the prosthesis, the catheter parts covering it and the introducing means like introduction port, or introducer sheath etc. are designed and worked in very precise dimensions and are thus prone to malfunction in case of not matching dimensions or minimal damage of the parts which are close and precise aligned with each other like e.g. an outer shaft covering a prosthesis and aligning with the delivery system tip. Damage to the catheter parts may occur due to the difficulty the operator will experience in the course of loading the prosthesis onto the catheter and repeated failure and repeated contact of his hands, the prosthesis and the shaft. More so, if three or more eyelets are to be introduced into receiving means of the catheter and capsule carrying the prosthesis and one after the other eyelet or all in one attempt shall be covered by the shaft it may be necessary to bend and twist the shaft over the eyelets and thus the edge of the shaft will be potentially widened and change its dimensions. This will lead to bent or uneven edges and lead to incorrect alignment of the different parts involved leading to a malfunction as described above. The more connecting means and receiving means are involved the higher the risk of damages and complications during the medical procedure which will follow.

The loading procedure is a difficult and usually manual task. The correct placement and connection with the delivery system is often difficult because of the flexibility of the stent or prosthesis. The stent or prosthesis is to be attached at several points and often one part detaches while another part is connected with the delivery system.

One object is thus to provide a device and a procedure which has less impact on the parts of the catheter and prosthesis involved, and which is less damage prone than known devices and procedures.

One object underlying the current application was thus to facilitate the loading procedure and to reduce or essentially avoid the disadvantages of prior art loading procedures.

SUMMARY OF THE DISCLOSURE

In one aspect the disclosure relates to a connecting device comprising receiving means carried by a receiving means holder for receiving a connecting means of a medical device and means for accelerating the introduction of the connecting means into the receiving means.

In another aspect the disclosure relates to a method for loading a prosthesis onto a delivery device comprising the steps: A. introducing a first connecting means of a medical device into a receiving means positioned on a delivery system, introducing a second connecting means of said medical device into a receiving means positioned on a delivery system, optionally introducing another connecting means of a medical device into a receiving means positioned on said delivery system, B. connecting the remaining medical device on said delivery device, C. optionally performing further crimping actions.

In yet another aspect the disclosure relates to a device comprising a connecting device as described herein comprising at least an inner shaft to which the connecting device is connected, and an outer shaft capable of maintaining a stent or replacement heart valve prosthesis in a compressed state.

In yet another aspect the disclosure relates to a system comprising a stent or a medical device or a replacement heart valve prosthesis and a delivery system useful for minimally invasive or a transcatheter delivery of said stent, device or prosthesis comprising a receiving means carried by a receiving means holder for receiving a connecting means of a medical device and means for accelerating the introduction of the connecting means into the receiving means.

In yet another aspect the disclosure relates to a method for delivery and/or deployment in one step or by way of sequential release.

In yet another aspect the disclosure relates to a method for retrieval of a fully released medical device wherein a connecting device as described herein is applied.

BRIEF DESCRIPTION OF THE DRAWINGS

The Figures will illustrate the disclosure and represent illustrative embodiments of the disclosure without to be understood restricting in any way.

DETAILED DESCRIPTION

Figure 1:
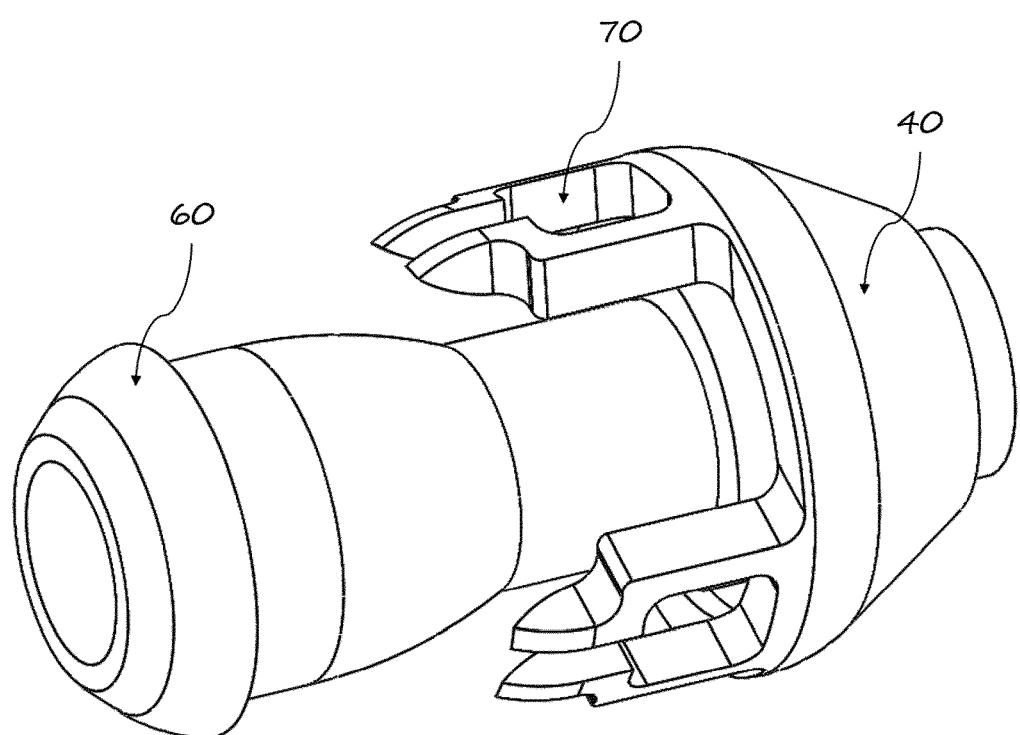
FIG. 1 describes a connecting device wherein receiving means (70) are positioned around one side of a receiving means holder (40) and a core (60).
Figures 2A, 2B:
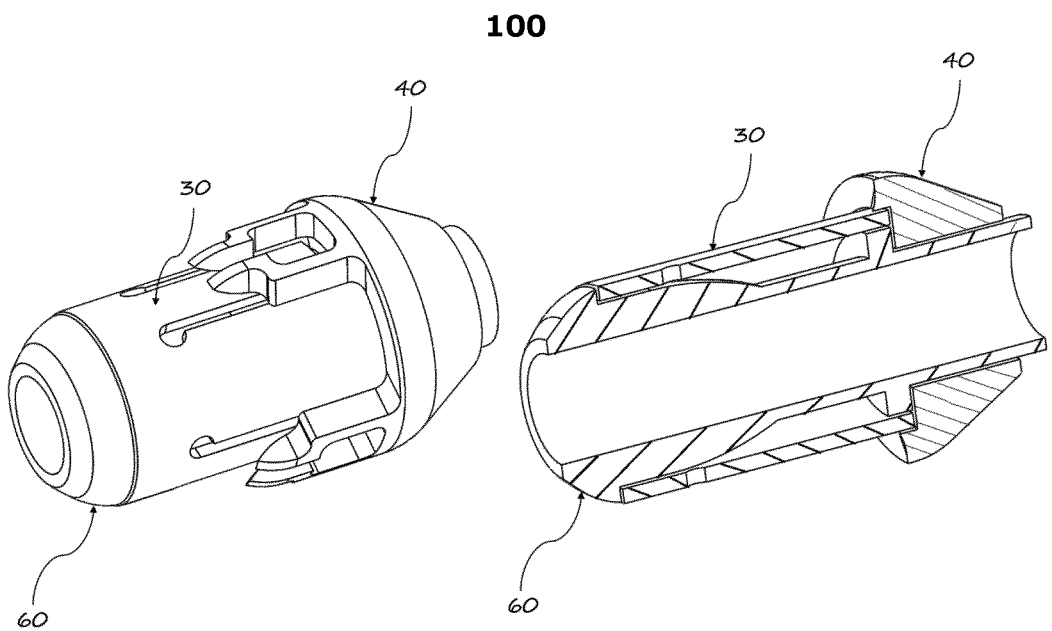
FIG. 2*a* illustrates a connecting device wherein a leaf spring (30) and core (60) are shown aligned with the receiving means positioned on the receiving means holder (40)
FIG. 2*b* illustrates a connecting device cross-sectional view wherein a space is shown underneath the leaf spring (30) and core (60).
Figure 3:
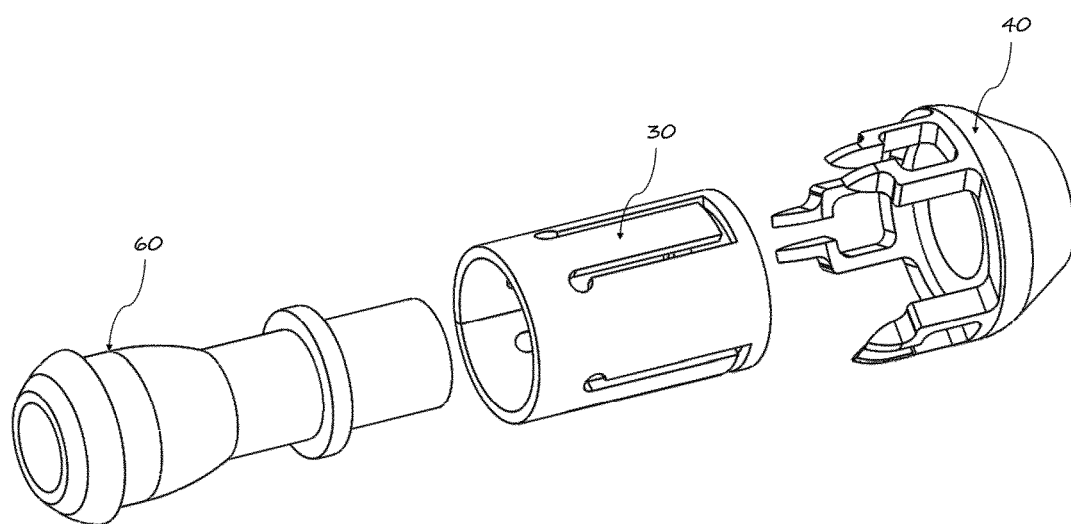
FIG. 3 shows an exploded view wherein core (60), the part with the means for accelerating the introduction of the connecting means, here a leaf spring (30) is shown and receiving means holder (40) with the receiving means.
Figure 4:
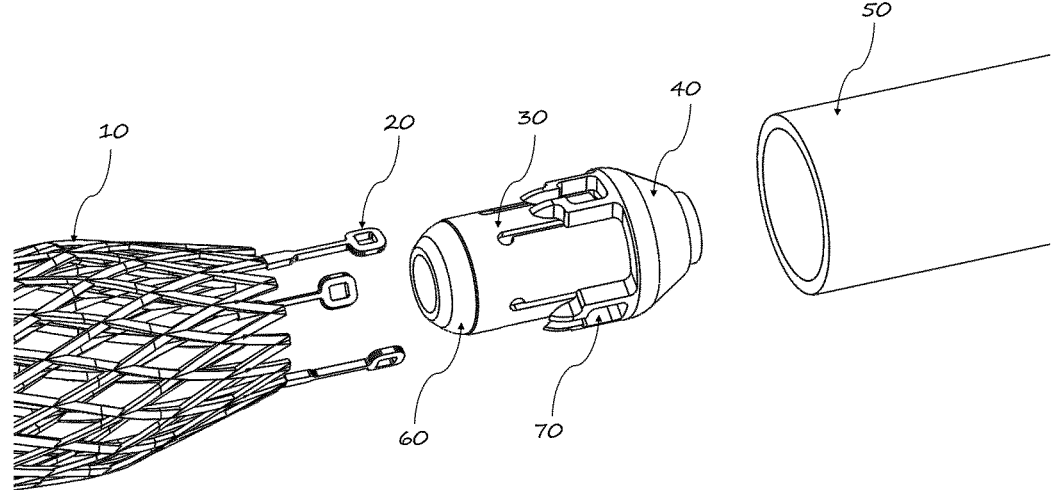
FIG. 4 in addition to FIG. 1, 2, 3 shows a shaft (50) and an exemplary medical device (stent) (10) comprising connecting means (20), in this case eyelets, wherein the stent is not yet connected with the stent holder comprising core (60), receiving means holder (40), leaf spring (30), and receiving means (70). The loading procedure comprises the steps wherein the eyelets (20) are introduced into receiving means (70) through pushing the eyelet in direction of the receiving means (70) wherein the eyelet pushes the leaf spring (30) inside. At this stage the shaft (50) will be positioned to cover the receiving means (70) and to protect the eyelets (20) from early release. In the next step the eyelet (20) will engage with the receiving means (70) simultaneously or one eyelet (20) after another from underneath. As soon as one or more eyelets reach the correct position underneath the eyelet pockets of the receiving means the permanent pressure of the leaf spring will press the eyelet from inside to outside into the open space of the receiving means. The shaft (50) will be pushed partially or essentially completely over the receiving means holder (40) and thus the self-expanding stent (or any self-expanding prosthesis) will be kept in its crimped state with the eyelets (20) in the receiving means (70). The shaft (50) has to be positioned in a manner in order to cover the receiving means (70) before any of the connecting means (20) will be introduced into any receiving means (70). Thus it is possible to engage one eyelet (20) after the other without the need of holding the other eyelets (20) while engaging the other eyelets (20) into the stent holder. One advantage of the invention is that the connecting means (20) are pushed into the receiving means (70) from the inside and that the accelerating means will push the connecting means (20) from inside to outside until the level where either the catheter shaft will block further outward movement of the self-expanding stent due to a partial or essentially complete covering of the receiving means by the shaft or alternatively by way of a loading tube. Thus all parts of the catheter, and in particular the shaft, advantageously are not exposed to manual manipulation and thus damage thereto is avoided.
Figure 5:
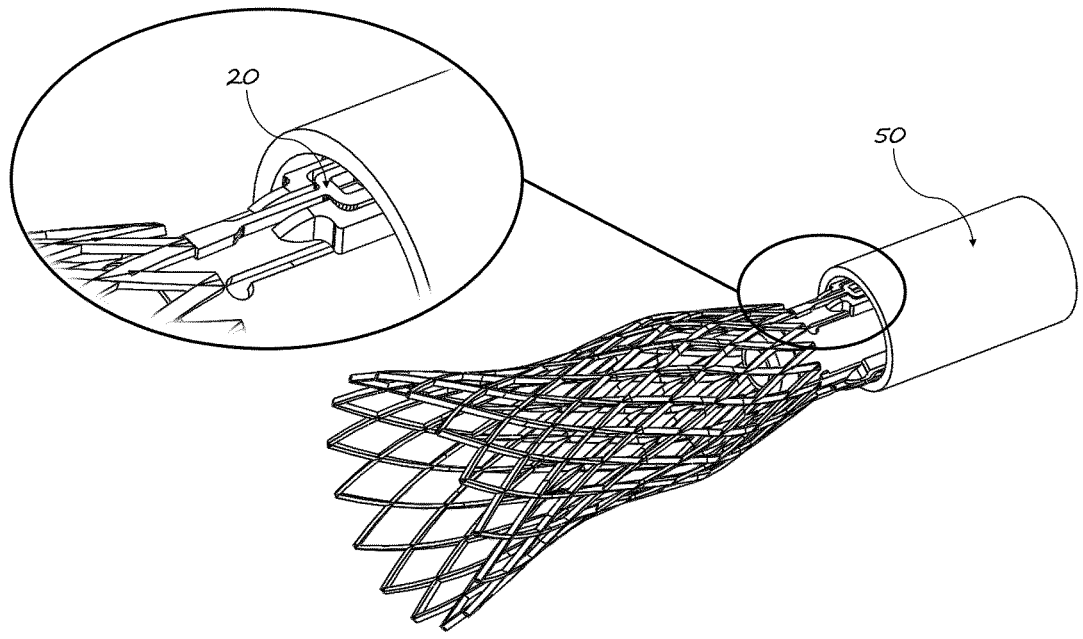
FIG. 5*a* is a blow up (detail view) of FIG. 5*b* wherein a shaft (50) of a catheter (or in general a delivery system) is depicted which is positioned (pushed over) over a stent (or prosthesis) holder and in particular pushed or positioned so far over the stent holder that the connecting means (20) stay protected in the receiving means and thus the stent or prosthesis is crimped from an expanded state into a compressed state and connected with a delivery system useful for minimally invasive delivery, e.g. by transfemoral delivery. The function of outer shaft (50) can also be achieved by an independent circumferential ring or means capable of covering the receiving means. Such a retaining means can be independently actuated by an independent mechanism and which mechanism can possibly be linked to the outer shaft (50).
Figure 6:
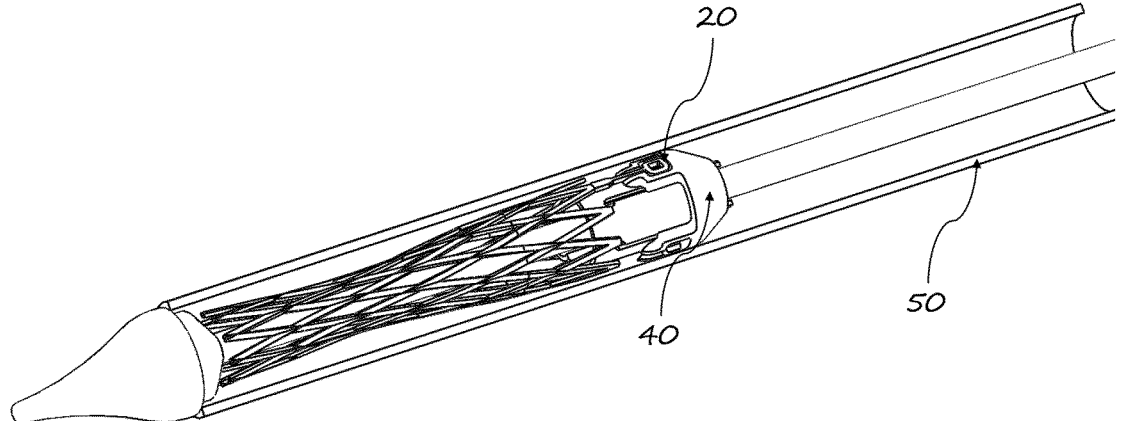
FIG. 6 illustrates a stent (10) (which can also be a heart valve replacement device wherein the sealing and valve is not shown and which prosthesis may be a mitral, tricuspid or any other heart valve replacement) which is crimped to a compressed state and engaged by way of eyelets (20) with the receiving means positioned at the receiving means holder (40) (forming part of the stent holder) wherein the shaft (50) is placed outside and over the stent. The shaft (50) thus keeps the stent in a compressed state and engaged with the receiving means. The receiving means can also be denoted as a crown. As shown here the shaft (50) extends to the tip of the catheter (delivery system). The distal part of the catheter can comprise a flexible tip. The shaft (50) can also be denoted outer shaft of the catheter. The shaft (50) can be pushed and eventually brought into alignment with a counter means comprised by the tip of the catheter. The outer shaft (50) depending on the particular embodiment can cover the stent completely or only partially.
Figure 7:
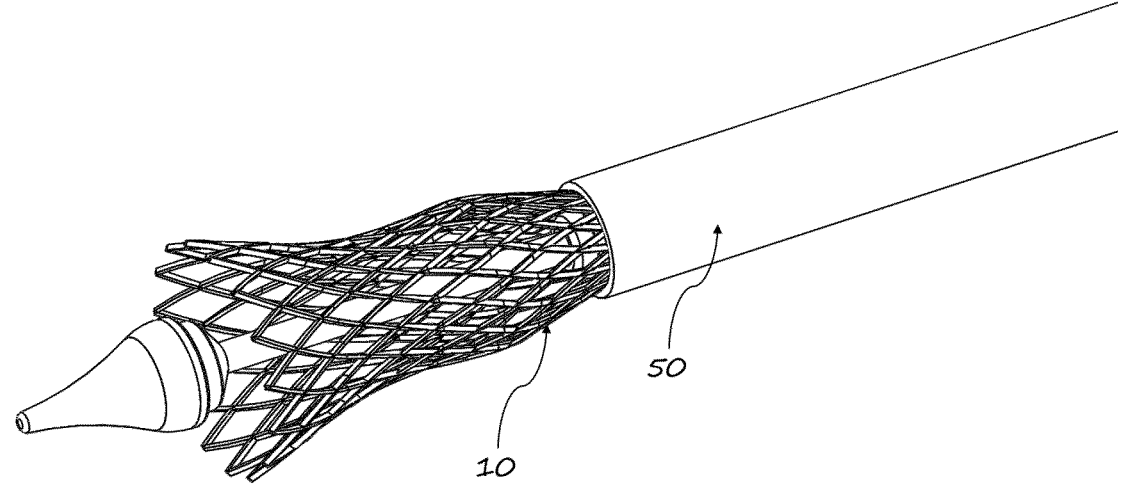
FIG. 7 illustrates a stent (or prosthesis as defined above) (10) partially crimped or in the process of loading to or release from the delivery system. In the process of loading/release the shaft (50) is pushed distally over the stent or pulled proximally from the stent (10) and thus the stent (10) is only partially covered and is either compressed during the process of loading or expanded during the release/deployment process.
Figure 8:
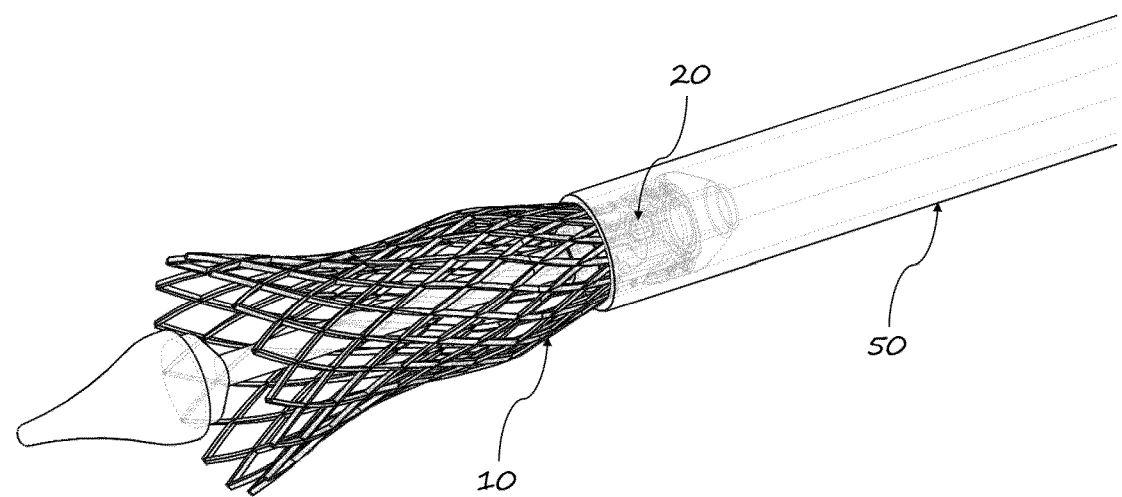
FIG. 8 resembles FIG. 7 wherein the parts covered by the shaft (50) are visible, i.e. the inner catheter shaft and the connecting means (20) engaged with the receiving means.
Figure 9:
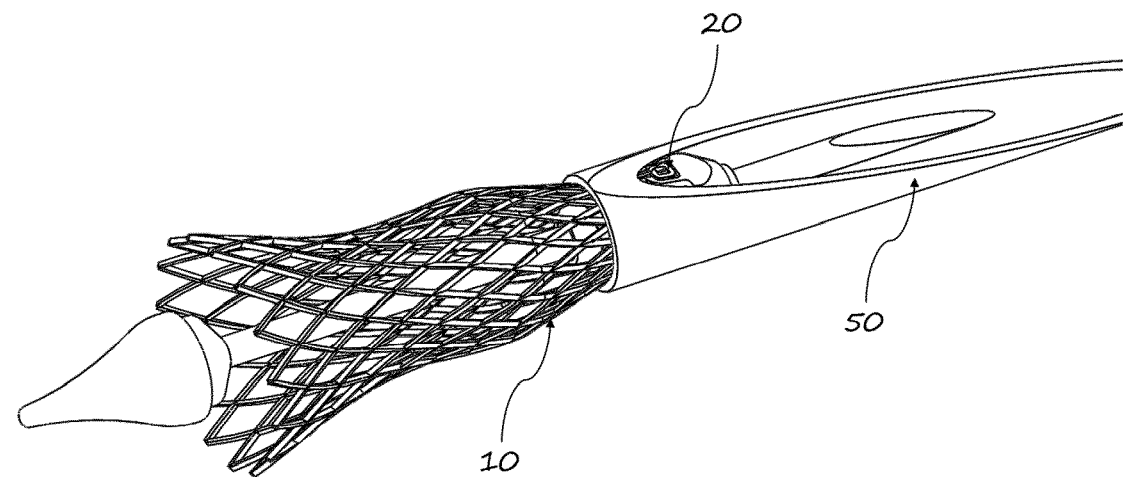
FIG. 9 shows further details of FIGS. 7 and 8 with the detail of the engagement of the eyelet (20) with the receiving means and the inner shaft of the catheter onto which the stent holder is attached. The eyelet (20) of the stent is shown engaged with receiving means and covered by outer shaft (50) and thus keeping the stent in a compressed state in the areas covered by shaft (50).
Figure 10:
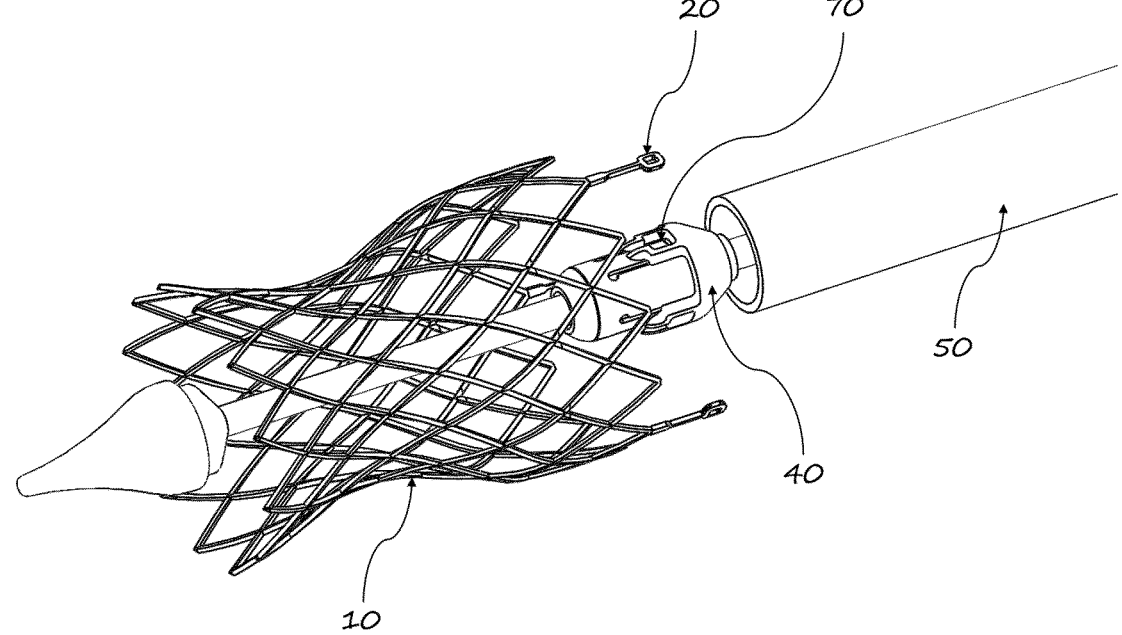
FIG. 10 illustrates a system comprising a stent (or a heart valve replacement prosthesis) and a delivery system; the delivery system comprises a stent holder comprising a receiving means holder (40) comprising three receiving means (70) (the third receiving means is not visible) and a core mounted onto an inner catheter shaft and further comprising a tip comprising a receiving means for the stent and an outer shaft (50); the stent comprises three eyelets (20) (the third eyelet is not visible). The stent is in its expanded state and thus this figure illustrates the system either before the stent is crimped to its compressed state and engaged with and loaded onto the catheter, or in its expanded state after release from the catheter during the deployment procedure.
Figure 11:
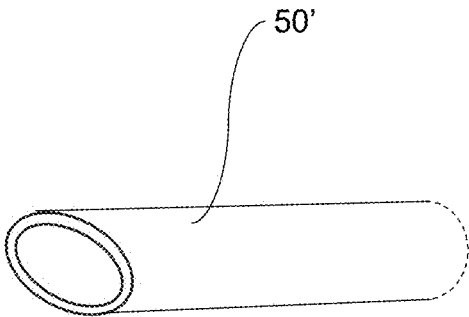
FIG. 11 illustrates an outer shaft having an asymmetric design.

In the following certain terms of the disclosure will be defined while terms not defined herein are to be understood in the sense the skilled person in the applicable field will understand such technical terms.

A "stent holder" in the sense of the disclosure is a means which will engage a part of a stent or prosthesis during the process of crimping and which will hold the stent or prosthesis during the delivery procedure until the stent or prosthesis is released and deployed at a target site. A stent holder may comprise a core, a receiving means holder, one or more accelerating means, one or more receiving means, and/or other parts or means useful in the context of the disclosure.

A "means for accelerating the connection or/and introduction of the connecting means" or "means for accelerating" in the sense of the disclosure is a means which supports the releasable connection of a connecting means with a receiving means; such a means can be e.g. a spring leaf. A "means for accelerating the connection or/and introduction of the connecting means" has a certain degree of flexibility and can e.g. be pushed in one direction and will return to its primary position and support the engagement of a connecting means with a receiving means. During the procedure of connecting one connecting means with its counterpart receiving means in one aspect the means for accelerating is pushed inwardly and upon engagement of the connecting means with its counterpart receiving means it is pushed outwardly again and thus holds the two parts connecting means and receiving means in a predefined position by blocking one side, e.g. the inner side. The shaft or loading tube will block the other side, e.g. the outer side, by being pushed partly or essentially over the receiving means. Thus the connecting means is introduced inside-out or from interior or from the central direction into the receiving means.

A "receiving means holder" in the sense of the disclosure is carrying at least two, three, four, five or more receiving means and may be forming a part of a stent holder.

A "receiving means" in the sense of the disclosure is a means capable of engaging with a connecting means; the receiving means can have a round or a quadrangular or square design or a triangular design and has a counter-shape with regard to a connecting means.

A "core" in the sense of the disclosure is a part that is connected to an inner shaft; the core can also be connected to or form one part with a receiving means holder and receiving means.

A "shaft" can be an inner or outer shaft of a catheter wherein the inner shaft can carry and be connected with a tip, a stent holder, other shafts, e.g. one or two outer shafts wherein the shafts can slide over one another. The functionality of the outer shaft can also be provided with respect to the loading procedure wherein the connecting means is involved by way of a loading tube which one may slide over the receiving means. The area of the end which interacts with the receiving means or which is to be pushed to the area or/and over the receiving means can have a uniform edge or the end of the shaft or leading tube may have a design which exhibits different edges with regard to the receiving means and thus the shaft or loading tube can be pushed stepwise over the connecting means when engaging with the receiving means and in one aspect of the disclosure can simplify the engagement procedure and the securing of the engagement of the receiving means with the connecting means.

A "stent" in the sense of the disclosure is a self-expandable stent which can be made of any useful material as steel, composite, or nitinol. A stent can be connected with other means or materials like artificial or natural tissue, e.g. porcine or bovine pericardium. The stent can be e.g. a laser cut nitinol stent.

A "heart valve prosthesis" or "replacement heart valve prosthesis" in the sense of the disclosure is a stent-based prosthesis comprising sealing and valve features wherein the materials can be chosen from polymers, or natural tissue like pericardial tissue.

A "medical device" in the sense of the disclosure is any medical device for delivery into a subject and wherein the delivery is performed by a catheter-based delivery system. A medical device in the sense of the disclosure can be a stent, a heart valve replacement prosthesis etc.

A "connecting means" in the sense of the disclosure is a means capable of engaging with a receiving means; the connecting means can have a round or a quadrangular or square or rectangular or triangular design and has a counter-shape with regard to a receiving means; it can be designed e.g. as an eyelet.

A "catheter" or "delivery system" is any system useful for minimal invasive delivery of a stent or prosthesis or replacement heart valve prosthesis comprising one or more shafts, a part for carrying a stent or a prosthesis, a handle for manipulating or actuating parts or means engaging the stent or prosthesis and other means known to the skilled person useful for a minimal invasive delivery and deployment of a stent or prosthesis. The catheter can also be a steerable catheter or a catheter which has a part or several parts which are steerable, i.e. one can manipulate the bending of the catheter tip of parts of the catheter shaft from the handle in order to more easily direct the tip to the target site.

The problem underlying the application is solved by an advanced version of a stent holder, a component commonly used in delivery systems, e.g. in transcatheter heart valve replacement systems. It serves the purpose to securely attach a stent/prosthesis, e.g. a heart valve replacement prosthesis, to the delivery system to ensure controlled release and to prevent premature deployment.

In one aspect the disclosure related to a connecting device which entails a
  receiving means carried by a receiving means holder for
    receiving a connecting means of a medical device and
    at least two means for accelerating the loading procedure.

During loading of the stent/prosthesis the delivery system outer shaft is advanced over the eyelet pockets of the connecting device and in particular over the receiving means to secure the engaged connecting means in the receiving means. The prosthesis to be loaded can e.g. comprise three eyelets wherein each eyelet is pressed down on the accelerating means, e.g. a leaf spring, to guide the eyelet into its receiving means, e.g. a pocket. The leaf spring continually presses the connecting means into the eyelet pocket of the receiving means and prevents the eyelet from collapsing inwards and the delivery system outer shaft pushed over the eyelets prevents the eyelets from expanding. With this technique each eyelet is engaged individually and subsequently with the connecting means.

The invention as disclosed herein solves the problem of having to engage all eyelets and maintain them in their position/recess at the same time while the delivery system shaft is advanced. The invention allows to engage each eyelet one at a time with the stent holder without the problem that eyelets may disengage. This is particularly useful the more eyelets the stent/prosthesis has.

The invention advantageously eliminates the problem of having to maintain all eyelets in their position on the stent holder at once while advancing the delivery system outer shaft.

In one aspect the disclosure relates to a connecting device comprising at least two receiving means (70) carried by a receiving means holder (40) for receiving a connecting means (20), e.g. an eyelet or a similar means for engagement, of a medical device, e.g. a stent or replacement heart valve prosthesis, and at least two means for accelerating the introduction (30) of the connecting means (20) into the receiving means.

The inventive connecting device advantageously supports an easy loading procedure and allows for a stepwise engagement of the stent (or prosthesis or medical device) with the delivery system. The inventive connecting device as disclosed herein prevents that a connecting means of a stent (or prosthesis or medical device) unintentionally disengages from the delivery system. Thus the loading procedure of a self-expanding stent (or prosthesis or medical device) is facilitated, is made more reliable and helps to reduce the implantation time for such a device. Overall, the connecting device as disclosed herein in an advantageous manner supports the safety of such medical devises and systems and thus overall improves the safety for patients who require such replacement devices.

More so, the device as disclosed herein provides for a harmless loading procedure of a stent to a catheter and for less damage prone components and thus will reduce operational complications during the medical delivery procedure.

The accelerating means can be any useful means to facilitate the connection of the connecting means of the stent or prosthesis to the catheter. Advantageously the connecting device as described herein comprises a connecting means (20) which is an eyelet of a medical device or/and the means for accelerating the introduction (30) is a leaf spring.

According to the current disclosure the accelerating means is characterized to be capable of engaging a connecting means of a stent, prosthesis or any medical device meant to be implanted into a subject by way of minimally invasive techniques and in addition prevent the unwanted or premature disengagement and release of the stent, prosthesis or medical device. In one aspect the accelerating means is capable of allowing the engagement of the connecting means with the receiving means, however, which does not allow the disengagement thereof. This is achieved by way of a mechanism which allows the connection of the connecting means and the receiving means only in one direction, however, does not allow functionally that the engaged parts connecting means and receiving means can disconnect each other unless a shaft or another means covering the receiving means is moved to allow the self-expanding stent to expand radially and thus disengage from the delivery system and in particular from the receiving means.

The invention thus advantageously has provided a simple solution to achieving a secured engagement of the stent or prosthesis with the delivery system.

It could be shown that in one advantageous embodiment the connecting device is characterized in that the connecting means (20) comprises three leaflet springs and three receiving means holders.

In one aspect the accelerating means has spring properties and it requires a gap to the core, which allows the leaf spring to be pushed downwards. The leaf spring can have varying dimensions as is useful in connection with the other device features. The length of the leaf spring can be about twice as long as the eyelet of the stent or prosthesis.

The means for accelerating the introduction (30) can be made of any useful material which is also compatible with the other materials of the device. The means for accelerating the introduction can be made of metal, plastic, or a composite material.

In the connecting device as disclosed herein the receiving means holder (40) is positioned around a core (60). The core can carry as many means for accelerating and in one embodiment the core (60) carries the at least one means for accelerating the introduction (30) of the connecting means (20).

In the connecting device as disclosed herein each cavity (70) is essentially aligned with each means (30) for accelerating the connection/introduction of the connecting means (20) into the receiving means (70).

At a certain stage of the loading procedure it is advantageous if at least one receiving means (70) is releasable covered by a shaft (50).

In another aspect the disclosure relates to a method for loading a prosthesis onto a delivery device comprising the steps: a. introducing a first connecting means of a medical device into a receiving means positioned on a delivery system, introducing a second connecting means of said medical device into a receiving means positioned on a delivery system, optionally introducing another connecting means of a medical device into a receiving means positioned on said delivery system, b. connecting the remaining medical device on said delivery device, c. optionally performing further crimping actions.

In another aspect the disclosure relates to a delivery device comprising a connecting device as described herein comprising at least an inner shaft to which the connecting device is connected, and an outer shaft capable of maintaining a stent or heart valve replacement prosthesis in a compressed state.

In another aspect the disclosure relates to a method for deployment of a medical device, preferably a replacement heart valve, using a delivery system wherein the medical device is released in one step or sequentially from the delivery system wherein one or several connecting means are released from the receiving means by way of movement of the outer shaft of the delivery system and in a second step withdrawal of the delivery system and complete release and deployment at a target site.

It can be advantageous if in said method at least one connecting means is maintained in at least one receiving means and the medical device can thus be retrieved before complete release from the delivery system.

The advantage can e.g. be achieved in that at least one connecting means is maintained in at least one receiving means due to a design variation of the maintained connecting means as compared to the other connection means released from the receiving means or due to an asymmetric design of the outer shaft whereby in a first step of movement all but one connecting means is released and in a second step the maintained connecting means can be released by way of an additional movement of the outer shaft. The shaft can have opening, or an asymmetric design which allows by way of e.g. openings or an asymmetric cut that all but one connecting means is released from the receiving means when the shaft is pushed or pulled depending on the overall design in a first step. Thus the openings will release all but one connecting means and hence the medical device can essentially fully expand itself and can be positioned at the target site and the positioning can be controlled by any useful visualizing means. In case of the need of repositioning the medical device, it can be again pulled back partially or fully into the delivery system and it can be repositioned. In such a case all connecting means have essentially the same design and can be also denoted to have a symmetrical design.

It is also possible to achieve a partial release of the medical device due to an asymmetrical design of the connecting means. E.g. in one of the connecting means the connecting means is longer than the other connecting means and thus the release and expansion of the self expanding medical device is facilitated. In this design variation such a medical device design may be combined with an asymmetrical design of the outer shaft to allow for partial release and retrievability of the medical device.

In another aspect the disclosure relates to a method for retrieval of a partially released or/and deployed medical device and/or retrieval from a target site wherein the medical device is visualized by way of an echo or other useful visualization means, and one or more connecting means of the medical device is introduced into the receiving means by way of manipulating the delivery system in the appropriate directions, and the medical device is at least partially or fully crimped onto the delivery system and optionally can be retrieved from the target site. The connection of the medical device and the delivery system is advantageously achieved by way of the connecting device as described above and in particular by way of an advantageous design using a means for accelerating the introduction of the connecting means into the delivery system also in an in vivo situation controlled by visualization.

REFERENCE LIST

10 Stent/heart valve prosthesis
20 Connecting means, e.g. eyelet
30 Means for accelerating the connection/the introduction of the connecting means into the receiving means, e.g. a leaf spring
40 Receiving means holder
50 Shaft
50' Shaft having an asymmetric design
60 Core
70 Receiving means
100 Connecting device

What is claimed is:

1. A connecting device comprising at least two receiving means carried by a receiving means holder for receiving a connecting means of a medical device and at least two means for accelerating the connection and/or the introduction of the connecting means with the receiving means, optionally 3, 4, 5, or 6 means for accelerating the connection and/or the introduction of the connecting means;
   wherein the means for accelerating the connection and/or the introduction is a leaf spring and wherein the receiving means allows the connecting means only in one direction to engage with the receiving means and the receiving means allows the connecting means only to disengage in a radial direction;
   wherein the leaf spring is radially inward relative to the receiving means holder;
   wherein the receiving means holder is positioned around a core,
   wherein the leaf spring is between the core and the receiving means holder and
   wherein the leaf spring, the core and the receiving means holder are components separable from each other,
   optionally, wherein the medical device is a prosthesis or a replacement heart valve.

2. The connecting device according to claim 1 wherein the connecting means is an eyelet of the medical device, and the leaf spring moves in an inward radial direction for receiving the eyelet.

3. The connecting device of claim 1, wherein the connecting device comprises three leaf springs and three receiving means, or 4, 5, or 6 leaf springs and 4, 5, or 6 receiving means,
   wherein each receiving means includes a pocket.

4. The connecting device according to claim 1, wherein the means for accelerating the connection and/or introduction is made of metal, plastic, or a composite material.

5. The connecting device of claim 1, wherein the core carries the at least two means for accelerating the connection and/or introduction, optionally 3, 4, 5, or 6 of the means for accelerating the connection and/or introduction.

6. The connecting device of claim 1, wherein each receiving means is aligned with a corresponding one of the means for accelerating the connection and/or introduction of the connecting means.

7. The connecting device of claim 1, wherein the at least two receiving means are releasable covered by a shaft or a loading tube.

8. A method for loading a prosthesis onto a delivery device including the connecting device of claim 1, comprising the steps of:
   a. introducing a first connecting means of the medical device into a first receiving means positioned on a delivery system, introducing a second connecting means of said medical device into a second receiving means positioned on said delivery system, optionally introducing another connecting means of the medical device into another receiving means positioned on said delivery system, optionally from inside to outside,
   b. connecting the remaining medical device on said delivery device, and
   c. optionally performing further crimping actions;
   wherein the device includes at least two means for accelerating the connection and/or the introduction of the connecting means with or into the receiving means,
   wherein the means for accelerating the connection and/or the introduction is a leaf spring, and
   the method includes:
   d. disengaging the connecting means from the receiving means in a radial direction.

9. A delivery device comprising the connecting device of claim 1, comprising at least an inner shaft to which the connecting device is connected, and wherein the outer shaft is capable of maintaining a stent or replacement heart valve prosthesis in a compressed state.

10. The connecting device comprising of claim 1, wherein the receiving means holder is for receiving a prosthesis or replacement heart valve and the at least two of the means for the introduction of the connecting means into the receiving means.

11. A method for deployment of a medical device, preferably a replacement heart valve prosthesis, using a delivery system wherein the medical device is released in one step or sequentially from the delivery system wherein one or several connecting means are released from the receiving means by way of movement of the outer shaft of the delivery system and in a second step withdrawal of the delivery system and complete release and deployment at a target site, wherein the method includes disengaging the connecting means from the receiving means in a radial direction;

receiving means is carried by a receiving means holder;

wherein the receiving means holder is positioned around a core, wherein a leaf spring is between the core and the receiving means holder and wherein the leaf spring, the core and the receiving means holder are components separable from each other.

12. The method according to claim 11 wherein at least one of the connecting means is maintained in at least one of the receiving means and the medical device can thus be retrieved before complete release from the delivery system.

13. The method according to claim 11, wherein at least one of the connecting means is maintained in at least one of the receiving means due to a design variation of the maintained connecting means as compared to the other connection means released from the receiving means or due to an asymmetric design of the outer shaft whereby in a first step of movement all but one connecting means is released and in a second step the maintained connecting means can be released by way of an additional movement of the outer shaft.

14. A method for retrieval of a partially released and/or deployed medical device and/or retrieval from a target site wherein the medical device is visualized by way of an echo or other useful visualization means, and one or more connecting means of the medical device is introduced into the receiving means and the medical device is at least partially or fully crimped onto the delivery system and optionally can be retrieved from the target site.

15. The method of claim 11, wherein the delivery system comprises a steerable shaft.

16. The connecting device of claim 2, wherein the connecting device comprises three leaf springs and three receiving means, or 4, 5, or 6 leaf springs and 4, 5, or 6 receiving means;

the means for accelerating the connection and/or introduction is made of metal, plastic, or a composite material; and the receiving means holder is positioned around a core which core carries the at least two means for accelerating the connection and/or introduction, optionally 3, 4, 5, or 6 of the means for accelerating the connection and/or introduction.

17. The connecting device of claim 16, wherein each receiving means is aligned with a corresponding one of the means for accelerating the connection and/or introduction of the connecting means; and the at least two receiving means are releasable covered by a shaft or a loading tube;

wherein the receiving means holder and the leaf spring are separable components and the receiving means is over the leaf spring, wherein contact between the leaf spring and the loading tube is avoided.

18. A delivery device comprising the connecting device of claim 17, comprising at least an inner shaft to which the connecting device is connected, and an outer shaft capable of maintaining a stent or replacement heart valve prosthesis in a compressed state.

19. The method of claim 12, wherein at least one of the connecting means is maintained in at least one of the receiving means due to a design variation of the maintained connecting means as compared to the other connection means released from the receiving means or due to an asymmetric design of the outer shaft whereby in a first step of movement all but one connecting means is released and in a second step the maintained connecting means can be released by way of an additional movement of the outer shaft.

20. The method of claim 19, wherein the delivery system comprises a steerable shaft.

* * * * *